United States Patent [19]

Koepff et al.

[11] Patent Number: 4,804,745

[45] Date of Patent: Feb. 14, 1989

[54] AGENTS FOR THE TREATMENT OF ARTHROSES

[75] Inventors: Peter Koepff, Heidelberg; Alexander Müller, Eberbach/Baden; Reinhard Schreiber, Eberbach/Baden; Angelika Turowski, Eberbach/Baden; Klaus Bräumer, Eberbach/Baden, all of Fed. Rep. of Germany

[73] Assignee: Deutsche Gelatine-Fabriken Stoess & Co. GmbH, Fed. Rep. of Germany

[21] Appl. No.: 68,342

[22] Filed: Jul. 1, 1987

[30] Foreign Application Priority Data

Jul. 25, 1986 [DE] Fed. Rep. of Germany ....... 3625185

[51] Int. Cl.[4] .................... G01N 33/54; C08F 220/32; A61K 39/385

[52] U.S. Cl. ....................... 530/356; 514/21; 514/100; 514/275; 514/370; 514/427; 514/2; 514/560; 514/801; 514/825; 514/859; 514/944; 530/356

[58] Field of Search ................. 514/21, 100, 275, 370, 514/427, 2, 560, 801, 825, 859, 944; 530/356

[56] References Cited

PUBLICATIONS

Krug, Von E., "Zur Unterstützenden Therapie bei Osteo- und Chondropathien", *Zeitschrift fur Erfahrungsheilkunde*, vol. 11, pp. 930–938.

*Primary Examiner*—John Kight
*Assistant Examiner*—Carlos Azpuru
*Attorney, Agent, or Firm*—Wegner & Bretschneider

[57] ABSTRACT

Agents for the treatment of arthroses contain peptides soluble in cold water, more specifically those from the group of hydrolyzed collagens. The peptides soluble in cold water are used for the treatment of arthroses and for the preparation of agents for the treatment of arthroses, respectively.

10 Claims, No Drawings

AGENTS FOR THE TREATMENT OF ARTHROSES

The present invention relates to agents for the treatment of arthroses which agents contain water-soluble peptides. Furthermore, the invention relates to the use of these water-soluble peptides for the treatment of arthroses and, eventually, to the use of these water-soluble peptides for the preparation of agents for the treatment of arthroses.

Degenerative joint diseases, conventionally known as arthroses are preferably found in bradytrophic tissue (tendon, cartilage) which is known to show poor blood flow or no blood flow at all and, due to its slow metabolism, is not capable of responding to external noxious influences either with inflammatory or with regenerative processes. The complaints occur more frequently among older people, however only because the average age of the population has increased and, thus, more people live long enough to experience arthroses.

However, with respect to pathogenesis of arthrosis it may be stated that they are by no means an inevitable phenomenon of ageing, since a normal joint is capable of functioning until a great age. Therefore, in medical science, a differentiation is made between socalled primary and secondary arthroses, the latter developing from connatal or acquired joint damages, i.e. from known precedent diseases, whereas in cases of primary arthroses no basic disease is determinable. These diseases rather manifest in a misproportion between mechanical stress and mechanical resistance of the joint cartilage.

In these cases predilection sites are formed by the weight-bearing joints, i.e. the hip and knee joints. In the loaded zone of these joints, the cartilaginous coating of the joint-forming portions is used up so that the subchondral bone is exposed and the unprotected bone surfaces get into frictional contact with each other. This is a slowly proceeding progressive process in which at first there are no troubles at all, whereas in a later stage, once the protective cartilage has been used up, serious troubles will arise.

The conservative treatment measures in the cases of coxarthroses and gonarthroses, respectively, and operative measures such as artificial joint prosthesis are sufficiently known.

It is the object of the present invention to provide agents for the treatment of arthroses which as much as possible have alleviating and curing effects on arthroses, while they are well compatible and readily received.

From empirical and clinical studies there ensued a suggestion that gelatin-containing preparations could play a supporting role in the therapy of degenerative joint diseases (Krug EHK 1979, 11).

Gelatin is a denatured collagen which is soluble only in hot water and upon cooling is capable of binding considerable amounts of water. For this reason it is used in a number of comestibles and drugs, however not as an active ingredient. The intake of larger amounts of gelatin is difficult to accomplish and, moreover, results in feeling of repletion and nausea.

Now, intensive clinical investigations have led to the surprising result that peptides soluble in cold water, and more specifically those from group of hydrolyzed collagens, are in fact suitable for the treatment of arthroses. Particularly suitable is an enzymatically hydrolyzed collagen having an average molecular weight of from 10 000 to 80 000 (10 to 80 kilodaltons). These hydrolyzed peptides may be well taken in the form of pastes, syrups, solutions, granules, compacts or instantized powder. Since they are almost flavorless or neutral in flavor, respectively, they may be particularly well taken in together with flavoring materials, sweeteners and/or aroma ingredients. Since for an efficient therapy daily doses of from 5 to 12 g have proven to be particularly effective, it is recommended to package the hydrolyzed collagens in dosage forms containing from 0.5 to 12 g of hydrolyzed collagen.

In the comparative clinical investigations is has been determined that a particularly good compatibility and intakeability, on the one hand, and a particularly good efficiency against arthroses, on the other hand, were observed when hydrolyzed collagens having an average molecular weight of from 10 000 to 80 000 (10 to 80 kilodaltons) were employed. Higher molecular weight preparations mostly are not sufficiently more quickly and readily soluble in cold water. Lower molecular weight products are more difficult to be brought into acceptable forms for application. Proteins not recovered from collagen have proven to be ineffective or substantially less effective.

Collagen is a fiber protein forming the main constituent of the supporting tissue and connective tissue in animals and humans and, more particularly, is found in the skin, the tendons and bones.

Thus, hydrolyzed collagen and, more specifically, enzymatically hydrolyzed collagen may be produced from animal skin, animal bones and other sufficiently purified connective tissue. Furthermore, it is basically possible also to employ a collagen having already been denatured (gelatin).

Hydrolysis can basically be effected by means of alkaline hydrolysis, acidic hydrolysis, pressurized hydrolysis or enzymatic hydrolysis. In each degradation the hydrolysis conditions may be chosen so that a defined molecular weight range is obtained. Depending on the preparation conditions, the hydrolyzates may have an excess of carboxyl groups or an excess of amino groups and possess different isoelectric pH ranges. Particularly mild conditions are those of enzymatic hydrolysis whereby particularly pure products containing low salt levels are obtained.

Such enzymatically hydrolyzed collagens are produced, for example, by Applicants and marketed under the designation of Gelita-Sol. These enzymatically hydrolyzed collagens mostly have an average weight of from 30 000 to 45 000 (30 to 45 kilodaltons). The molecular weight distribution ranges from 2 000 to 80 000 (2 to 80 kilodaltons). However, the major amount is within the range of from 5 000 to 40 000. These enzymatically hydrolyzed collagens are more or less flavorless or at least neutral in flavor. They are soluble in cold water and are no longer capable, as denatured collagen (gelatin) is, of binding significant amounts of water. However, they are well dispersible and emulsion-stabilizing. They also act in foam-stabilizing and cream-stabilizing capacities. They may be film-forming and may have adhesive properties.

They tend to form complexes with tensides and thereby improve the skin-compatibility of tensides. They improve the susceptibility to dry and wet combing and the shine of hair. They support digestion and are suitable of enveloping or embedding vitamins and aromas. Eventually they are used for improving the absorption of hair colorants and dyes for woolen fabrics.

In dietetics they have been used as general diet for gastric and intestinal diseases, indigestions, reduction diet, diabetes, but also as a build-up diet for athletes. Crucial therefor is the good digestibility of the protein, the protective colloid effect causative for a fine distribution of the nutrients and, thus, for an improvement of the digestibility of food altogether, a good binding property due to which meals may be prepared without using fat, the absence of carbohydrates and the absence of purine.

In the food sector they were used in the meat product industry, in the sweets and beverages industry. In pharmacy they were employed as tabletting aids, encasing agents and fillers. By means of the clinical investigations and double blind studies as now carried out it has been established that particularly these enzymatically hydrolyzed collagens in an amount of from 5 to 12 g per day have alleviating and curing effects on arthroses. Very surrising was the finding that already in the course of this therapy an analgesic effect was observed which gave rise to a clearly noticeable reduced need for other analgesics.

Thus, subject matter of the present invention first are agents for the treatment of arthroses which agents contain peptides soluble in cold water, more specifically from the group of hydrolyzed collagens, enzymatically hydrolyzed collagens having an average molecular weight of from 10 000 to 80 000 (10 to 80 kilodaltons) being preferred.

Furthermore, the invention relates to the use of these peptides soluble in cold water for the treatment of arthroses and to the use of these water-soluble peptides for the preparation of agents for the treatment of arthroses.

The agents according to the invention, the preparation thereof and the use thereof are illustrated in greater detail.

EXAMPLE 1

Enzymatically hydrolyzed collagen was prepared by cutting, washing and enzymatically hydrolyzing fresh ox connective tissue or fresh pig skin in a tank fitted with a stirrer, inactivation of the enzyme, separation, filtration, re-concentration, sterilization and spray-drying. The product is a bright yellow to whitish powder which is soluble in cold water, neutral in flavor or almost flavorless and have particle sizes of less than 0.5 mm. The respective commercial products are Applicants' Gelita-Sol D (dietetics) and P (pharmacy). The average molecular weight was 40 000 and 60 000 (40 to 60 kilodaltons), respectively.

Both powders when wetted with some water may be compressed to form tablets which are readily redissolved in water as well as in gastric juice.

For easier intakeability, tablets of 0.5 g each were prepared, 10 to 24 of which may be taken ad libitum distributed over a day.

Larger amounts may also be applied in the form of pastes, syrups, solutions, granules, compacts or instantized powders, while ready-to-use instant beverages or instant soups may also be employed.

EXAMPLE 2

The following double blind study was carried out: Tablets containing 0.5 g of enzymatically hydrolyzed collagen according to Example 1 were used in comparison to corresponding tablets containing 0.5 g of gelatin powder or 0.5 g of proteins from hen's egg white. 81 patients were examined, 29 of whom had to discontinue the treatment for various reasons. The remaining 52 patients (24 females, 28 males) are relevant to the present study.

The collective of patients comprised cases of diseases of the degenerative type of the hip and/or knee joint, 10 test persons suffering from an unilateral coxarthrosis and 31 test persons showing degenerative alterations of both hip joints. 21 patients suffered from a marked arthrosis of the knee joints, in 6 cases both knee joints having been affected. Degenerative diseases of the hip and knee joints were found in 10 test persons. In more than half of the test persons the diseases had already lasted for more than 5 years, and only about 10% had suffered for less than two years.

The diagnosis was established by means of roentgenology, the cases being osteoarthroses of from the first to the third stages. As is shown in Table 1, in all of the 52 patients there was evidence that the joint cleft had undergone contraction. Under clinical aspects all cases were cases of an activated form of arthrosis. A subchondral sclerosing existed in 28 cases. Osteophytes were found in 41 patients, cysts were found in 10 patients, and erosions were found in 3 patients. Six patients already exhibited a *Protrusio acetabuli*.

In the clinical study the following subjective troubles were included as criteria for the evaluation of the tested substances:

Initial pain
Initial stiffness
Weakness
Sensitivity to cold
Pain under physical stress
Fatigue pain
Muscle pain
Night pain
Sensitivity to weather conditions
Pressure sensitivity over the joint cleft
Pressure sensitivity at the trochanter
Pressure sensitivity at the tendon onsets
Motion pain
End phase pain The motility of the affected joints was determined in a conventional manner by measuring the angle between the base and end positions in all physiological levels. The average motility of all examined joints is apparent from Table 2.

The subjective criteria listed in Table 2 were assessed in a two-stage test according to the patient's statement to be moderate (1 point) or well marked (2 points). From the initial score as thus obtained the score as newly determined after one treatment cycle of each test substance was deducted.

Moreover, the following laboratory tests were carried out:

Erythrocyte sedimentation rate after 1 hour and after 2 hours
Transaminases
Alkaline and acidic phosphatases
Antibodies in the serum against type I, type II, type III collagens Test substances The following substances were employed:
Test substance No. 173—Gelita-Sol D (according to the invention)
Test substance No. 174—Protein from hen's egg white Test substance No. 175—Gelatin powder (special grade for diet purposes)

Each of the three substances as indicated were applied in optional sequence for 60 days, respectively, with an interval without treatment of about 2 months prior to the next intake. Administered were 10 g of substance per day in the form of 20 pieces of tablets 0.5 g in weight each which could be taken by the patients in optional distribution during the day.

The administration of antiarthrotics (e.g. Arumalon or Arteparon) was deliberately avoided during the period of under investigation, whereas analgetics were allowed to be further taken with simultaneous dosage control (see Table 4).

Results

The investigation was started with a collective of 81 patients, 29 of which discontinued the treatment for various reasons. Six patients reported a discomfortable stomach pressure caused by preparation No. 175; four patients felt so well that they declined further intake of the test substances, while to the other patients (15) there occurred noxiousnesses of different kinds such as apoplexy of heart, hepatitis, carcinoma. Here, any relation to the administration of the test substances is not to be recognized.

With the remaining 52 patients the following results were obtained:

Transaminase/Phosphatase

The blood level in the test persons was normal and also remained constant during the whole period of investigation.

Erythrocyte sedimentation rate (BSG)

In the beginning of the test the BSG values were normal to slightly increased; on the average they were 11/1 h and 24/2 h. The highest acceleration was 20/42. During the test period a relevant change in the values was not determined.

Antibodies

The average values of the contents of antibodies against collagen were:
Against type I—4.357 (−log2)
Against type II—3.642 (−log2)
Against type III—4.07 (−log2)

The antibody titre underwent only insignificant changes during the administration of the test substances.

Evaluation of the results

Upon completion of the tests for each test substance the score was calculated and compared to the initial score. As will be apparent from the Tables 3 and 4, although the best results were accomplished with the test substance No. 175, said preparation frequently resulted in the "side effect" of a feeling of repletion. In 30 patients the terminal score after the administration of No. 175 was reduce by more than 50%. Only for 10 test persons the reduction from the initial, score was 25% or less. Test substance No. 173 basically showed very similar values. However, the differences from substance No. 174 were significant. By using this latter substance only an insignificant influence on the ailment symptoms was determinable, which fact is also evident from the minor decrease in the initial score which, namely, with 40 patients was not more than 25%.

The 12 patients exhibiting a reduction in the initial score in excess of 25%, prior to the administration of No. 174 had already taken the two other substances of the test program. In an another trial with an exclusive administration of the test substance No. 174, the reduction in the initial score was lower than 25% for all of the test persons without exception.

Table 4 contains the reduction in the administration of analgesics in the end of each test cycle with the respective test substance, measured in per cent. Also here, as in Table 3, the test substances No. 173 and 175 came out best, whereas No. 174 did not cause such a drastic decrease in the need for analgesics.

As positive marginal observations, for some patients during the cure weight reductions could be noted. Furthermore, alleviations from troubles of the spinal column and an improvement in the general condition of well-being were reported, so that some patients even requested the therapy to be continued. Also in these observation the test substance No. 175 showed the most significant effect, closely followed by No. 173.

X-ray examination

Roentgenologic changes could be determined neither in the positive nor in the negative directions.

TABLE 1

Osteoarthrosis
Roentgenologic criteria with 52 test persons prior to the beginning of the study

| | |
|---|---|
| Joint cleft contraction | 52 |
| Subchondral sclerosing | 28 |
| Osteophytosis | 41 |
| Cysts | 10 |
| Erosions | 3 |
| *Protrusio acetabuli* | 6 |

TABLE 2

Criteria prior to the administration of the test substances

| | positive findings |
|---|---|
| Initial pain | 44 |
| Initial stiffness | 45 |
| Weakness | 21 |
| Sensitivity to cold | 20 |
| Pain under physical stress | 52 |
| Fatigue pain | 52 |
| Muscle pain | 34 |
| Night pain | 24 |
| Sensitivity to weather conditions | 24 |
| Pressure sensitivity over the joint cleft | 48 |
| Pressure sensitivity at the trochanter | 25 |
| Pressure sensitivity at the tendon onsets | 29 |
| Motion pain | 17 |
| End phase pain | 52 |
| Motility of the hip joints (average) | |
| Flexion | 72° |
| Abduction | 16° |
| Internal rotation | 6° |
| External rotation | 16° |
| Motility of the knee joints | |
| Flexion | 92° |

TABLE 3

Score change after the administration of the test substances

| Test substances | Reduction in the initial score by | | |
|---|---|---|---|
| No. | >50% | 25-50% | <25% |
| 173 | 25 | 17 | 10 |
| 174 | 5 | 7 | 40 |

TABLE 3-continued

Score change after the administration of the test substances

| Test substances | Reduction in the initial score by | | |
|---|---|---|---|
| No. | >50% | 25-50% | <25% |
| 175 | 30 | 15 | 7 |

TABLE 4

Reduction in the administration of analgesics in the end of each test cycle using the test substance as set forth

| Test substances No. | >75% | 51-75% | 26-50% | <26% |
|---|---|---|---|---|
| 173 | 21 | 15 | 9 | 17 |
| 174 | 4 | 14 | 23 | 11 |
| 175 | 23 | 16 | 7 | 6 |

What is claimed is:

1. A composition for the treatment of arthroses comprising a peptide soluble in cold water having an average molecular weight of from about 10,000 to 80,000.

2. A composition of claim 1, wherein said peptide is hydrolyzed collagens.

3. A composition of claim 2, wherein the composition is administered in the form of a paste, syrup solution, granule, compact or instantized powder.

4. A composition of claim 2, wherein the composition contains one or more flavoring agents, sweeteners, aroma ingredients or combination thereof.

5. A composition of claim 2, where 0.5 to 12 g of said hydrolyzed collagen is administered to a patient.

6. A method for the treatment of arthroses comprising administering to a patient suffering therefrom a composition which comprises an effective amount of a hydrolyzed collagen, said hydrolyzed collagen being soluble in cold water.

7. A method of claim 6, wherein said hydrolyzed collagen has a molecular weight of from about 10,000 to 80,000.

8. A method of claim 6, wherein the composition is administered in the form of a paste, syrup, solution, granule, compact or instantized powder.

9. A method of claim 6, wherein the composition contains one or more flavoring agents, sweeteners, aroma ingredients or combination thereof.

10. A method of claim 6, wherein 0.5 to 12 g of said hydrolyzed collagen is administered to said patient.

* * * * *